(12) United States Patent
Kimpel, Jr. et al.

(10) Patent No.: US 10,175,149 B2
(45) Date of Patent: Jan. 8, 2019

(54) PIPE OUTER SURFACE INSPECTION APPARATUS

(71) Applicant: Aegion Coating Services, LLC, Conroe, TX (US)

(72) Inventors: Rick R. Kimpel, Jr., Conroe, TX (US); Randall L. Perkins, Houston, TX (US); Bryan Karasek, Huffman, TX (US)

(73) Assignee: Aegion Coating Services, LLC, Conroe, TX (US)

( * ) Notice: Subject to any disclaimer, the term of this patent is extended or adjusted under 35 U.S.C. 154(b) by 263 days.

(21) Appl. No.: 15/179,550

(22) Filed: Jun. 10, 2016

(65) Prior Publication Data

US 2016/0320266 A1 Nov. 3, 2016

Related U.S. Application Data (62) Division of application No. 14/213,631, filed on Mar. 14, 2014, now Pat. No. 9,389,150.

(Continued)

(51) Int. Cl.
| | |
|---|---|
| *G01B 21/30* | (2006.01) |
| *G01M 99/00* | (2011.01) |
| *F17D 5/00* | (2006.01) |
| *G01N 29/22* | (2006.01) |
| *G01N 29/265* | (2006.01) |
| *G01N 21/952* | (2006.01) |
| *G01B 7/06* | (2006.01) |
| *G01N 21/84* | (2006.01) |

(Continued)

(52) U.S. Cl.
CPC ............... *G01M 99/00* (2013.01); *F17D 5/00* (2013.01); *G01B 7/066* (2013.01); *G01B 11/0616* (2013.01); *G01B 21/08* (2013.01); *G01B 21/30* (2013.01); *G01N 21/8422* (2013.01); *G01N 21/952* (2013.01); *G01N 29/225* (2013.01); *G01N 29/265* (2013.01); *G01N 2021/8427* (2013.01); *G01N 2291/2634* (2013.01)

(58) Field of Classification Search
CPC ....................................................... G01B 21/20
See application file for complete search history.

(56) References Cited

U.S. PATENT DOCUMENTS

| | | | |
|---|---|---|---|
| 3,921,440 A | 11/1975 | Toth | |
| 4,331,034 A | 5/1982 | Takeda et al. | |

(Continued)

FOREIGN PATENT DOCUMENTS

| | | |
|---|---|---|
| CA | 2831812 A1 | 10/2012 |
| WO | 1995027170 | 10/1995 |
| WO | 2012129703 | 10/2012 |

OTHER PUBLICATIONS

International Search Report and Written Opinion of the International Searching Authority in related application PCT/US2014/028770 dated Oct. 13, 2014, 19 pages.

*Primary Examiner* — Robert R Raevis
(74) *Attorney, Agent, or Firm* — Stinson Leonard Street LLP (57) ABSTRACT

A pipe outer surface inspection apparatus. The apparatus may include a carriage adapted for turning on a pipe to be inspected and includes a pipe inspection head. The apparatus may include at least one of a surface profile gauge, coating thickness gauge, and coating holiday detector. The apparatus may include a pendulum encoder, a cable guard, and/or a magnetic fastener. Associated methods are also disclosed.

7 Claims, 12 Drawing Sheets

Related U.S. Application Data (60) Provisional application No. 61/793,458, filed on Mar. 15, 2013.

(51) Int. Cl.
  *G01B 21/08* (2006.01)
  *G01B 11/06* (2006.01)

(56) References Cited

U.S. PATENT DOCUMENTS

| | | |
|---|---|---|
| 4,434,660 A | 3/1984 | Michaels et al. |
| 4,722,142 A | 2/1988 | Schmidt |
| 4,974,168 A | 11/1990 | Marx |
| 5,069,234 A | 12/1991 | Nielsen |
| 6,243,661 B1 | 6/2001 | Baldwin et al. |
| 6,621,516 B1 | 9/2003 | Wasson et al. |
| 6,803,854 B1 | 10/2004 | Adams et al. |
| 7,077,020 B2 | 7/2006 | Langley et al. |
| 7,460,980 B2 | 12/2008 | Hinn |
| 7,656,997 B1 | 2/2010 | Anjelly |
| 7,786,415 B2 | 8/2010 | Thomas et al. |
| 7,952,485 B2 | 5/2011 | Schechter et al. |
| 7,970,734 B2 | 6/2011 | Townsend et al. |
| 2008/0300748 A1 | 12/2008 | Drummy et al. |
| 2010/0275694 A1 | 11/2010 | Roberts |

PIPE OUTER SURFACE INSPECTION APPARATUS

CROSS-REFERENCE TO RELATED APPLICATIONS

This application is a divisional of U.S. patent application Ser. No. 14/213,631, filed Mar. 14, 2014, which claims priority to U.S. Provisional Patent Application No. 61/793,458, filed Mar. 15, 2013, each of which is hereby incorporated by reference in its entirety.

FIELD OF THE INVENTION

The present disclosure generally relates to inspection of pipes, and more particularly to an apparatus for inspecting an outer surface of a pipe for conditions such as proper surface preparation prior to coating and/or proper coating application.

BACKGROUND OF THE INVENTION

Pipes of hazardous material conveying pipelines and other types of pipelines may be coated to protect the pipes from corrosion and increase their lifespan. Inspection of aspects of the pipe after it is prepared for coating and after the coating is applied ensures that desired coating specifications are met and the benefits of coating are realized. For example, a pipe may be prepared for coating by blasting to create a surface to which the coating can bond. The pipe may be inspected after this preparation step to determine if an adequate anchor profile for the coating was achieved by the blasting. After coating is performed, the coating may be inspected for discontinuities and/or desired thickness. Inspection of these aspects is particularly relevant in field coating, such as field coating of pipeline joints.

SUMMARY

One aspect of the present invention is directed to a pipe inspection apparatus including a carriage adapted for turning on a pipe to be inspected and including a pipe inspection head.

Another aspect of the present invention is directed to an automated pipe inspection apparatus including at least one of a surface profile gauge, coating thickness gauge, and coating holiday detector.

Another aspect of the present invention is directed to a pipe inspection apparatus including a pendulum encoder.

Another aspect of the present invention is directed to a pipe inspection apparatus including a cable guard.

Yet another aspect of the present invention is directed to a pipe inspection apparatus including a magnetic fastener for securing a portion of the apparatus on the pipe.

Other objects and features of the present invention will be in part apparent and in part pointed out herein.

BRIEF DESCRIPTION OF THE DRAWINGS

Corresponding reference characters indicate corresponding parts throughout the drawings.

DETAILED DESCRIPTION

Figure 1:
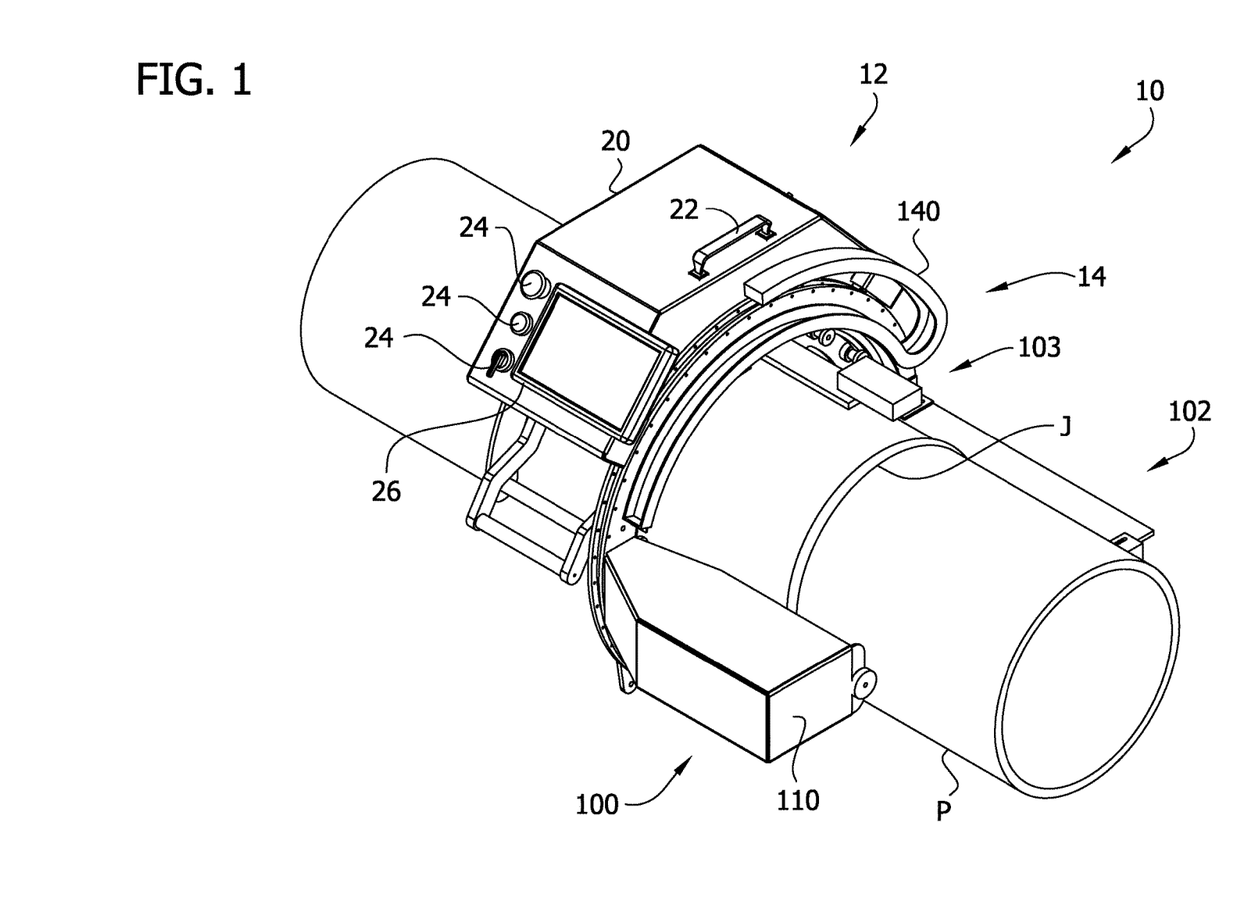
FIG. 1 is a perspective of a pipe inspection apparatus according to the present invention mounted on a pipe section.
Figure 2:
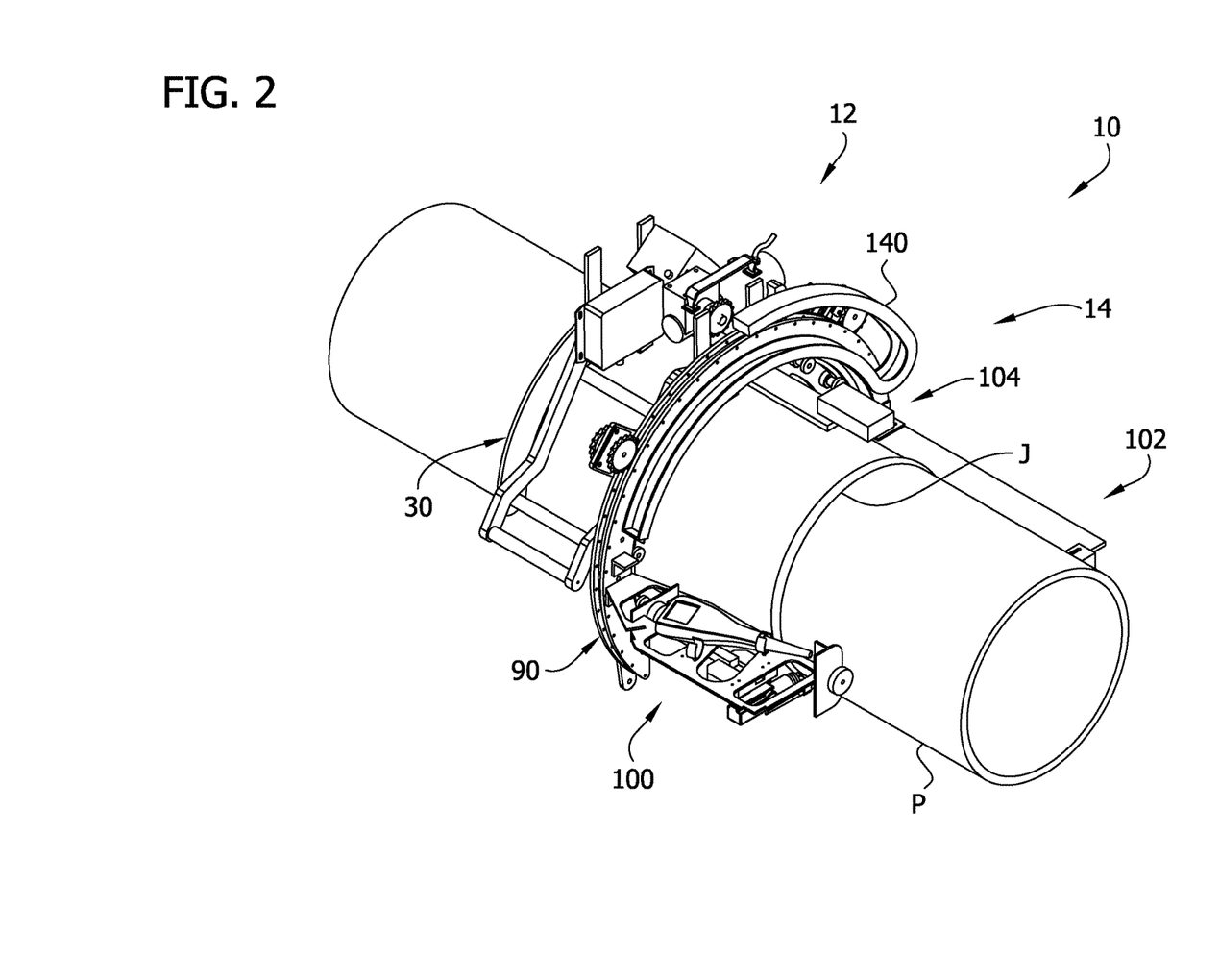
FIG. 2 is a view of the apparatus similar to FIG. 1 but having shrouds removed to expose interior components.

Referring to FIGS. 1 and 2, an outer pipe surface inspection apparatus according to the present invention is designated generally by the reference number 10. As will become apparent, the apparatus 10 is adapted for automated inspection of various aspects of an outer surface of a pipe. The apparatus 10 is modular for carrying inspection heads of various types. The apparatus 10 is configured for inspecting the full circumference of a pipe section. For example, the apparatus 10 may be used to inspect an anchor profile of the pipe surface after the pipe has been blasted in preparation for coating the pipe. The apparatus 10 may be used to inspect coating applied to the pipe for coating thickness and/or coating irregularities known as holidays. The apparatus 10 is particularly suited for inspecting the area of a pipe joint (e.g., a welded joint) for anchor profile and coating properties achieved while field coating the pipe joint. In FIG. 1, the apparatus 10 is shown mounted on a pipe section P including a joint J.

Figure 10:
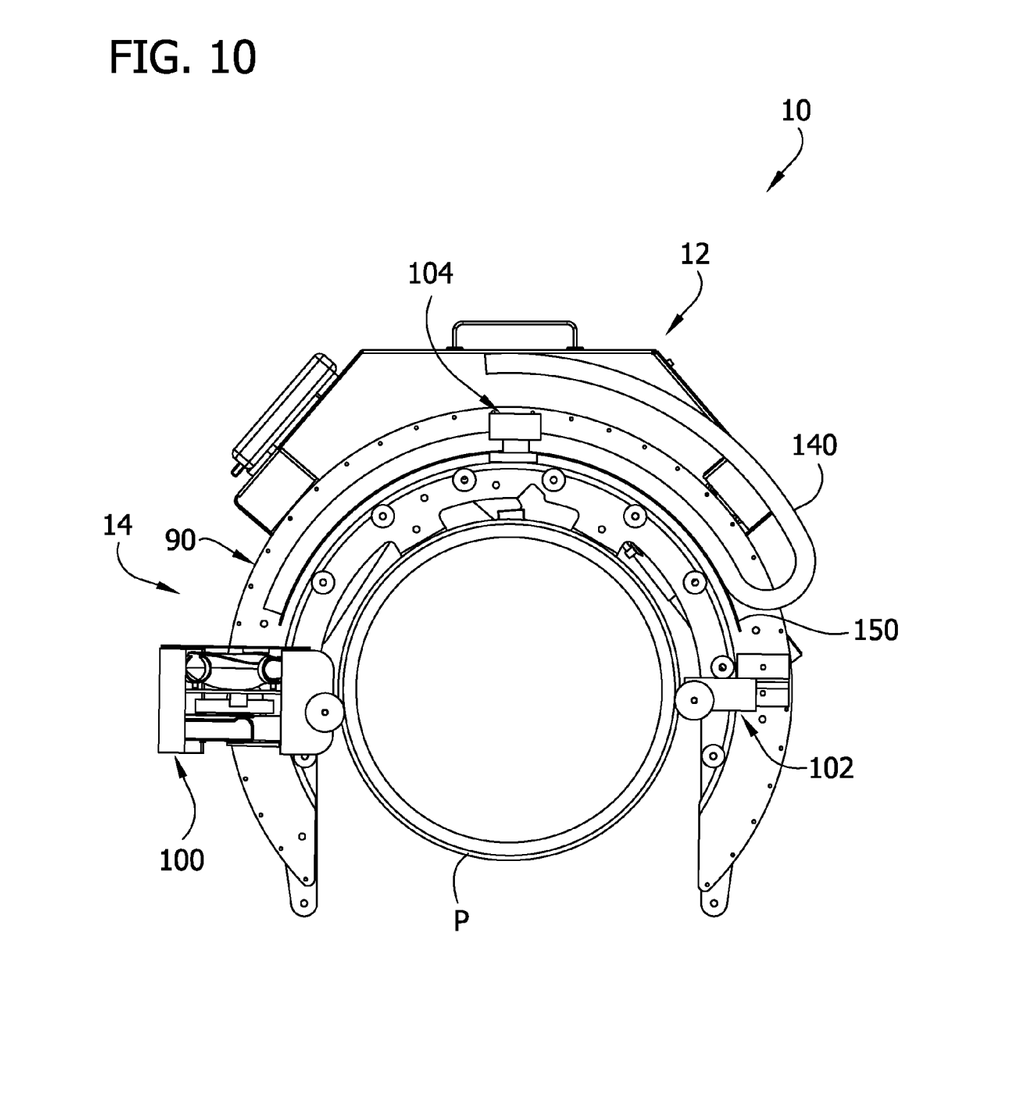
FIG. 10 is a front elevation of the apparatus and pipe section, the carriage being shown in a home position with respect to the base.
Figure 11:
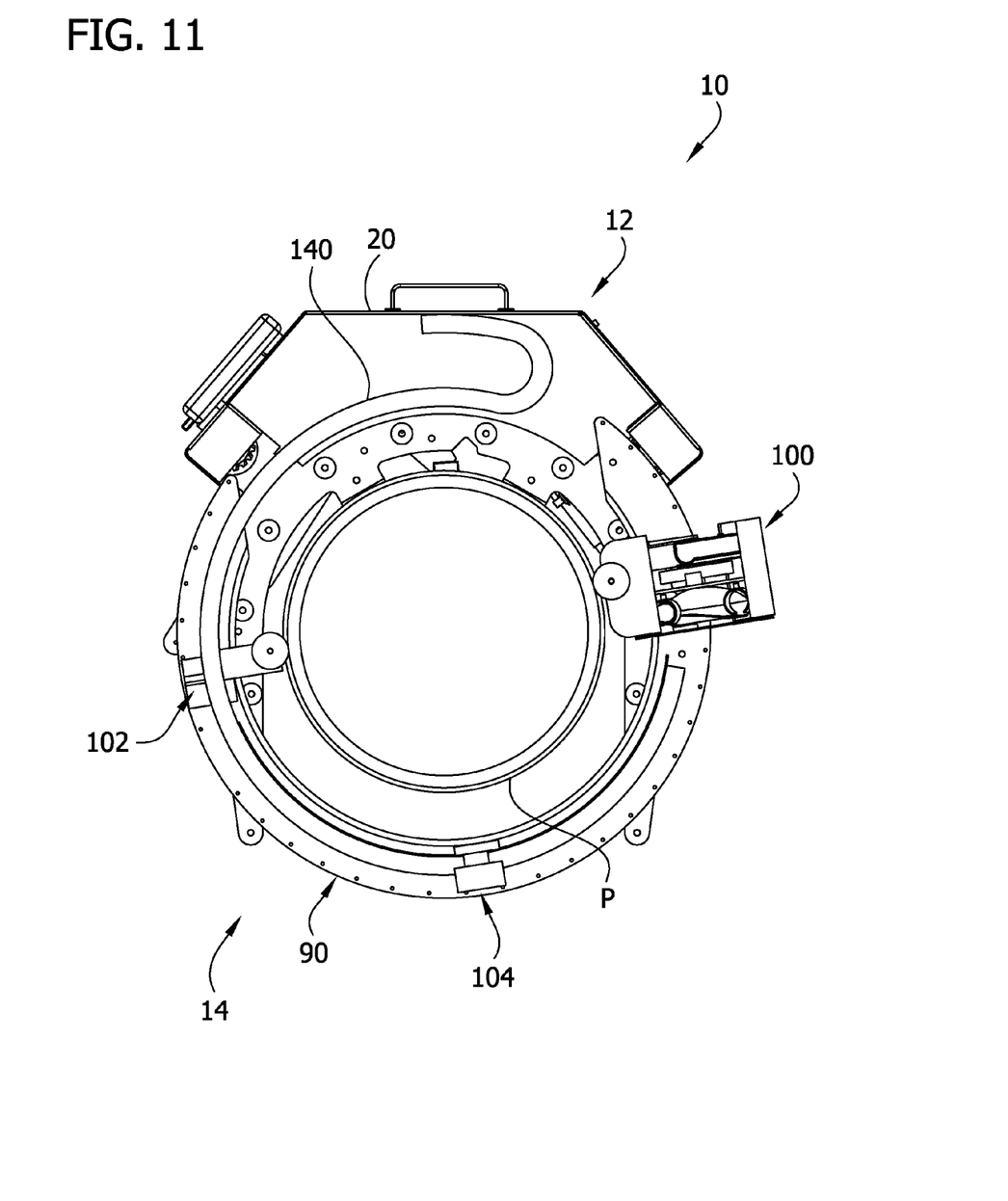
FIG. 11 is a view similar to FIG. 10 but showing the carriage rotated in a counterclockwise direction with respect to its home position.
Figure 12:
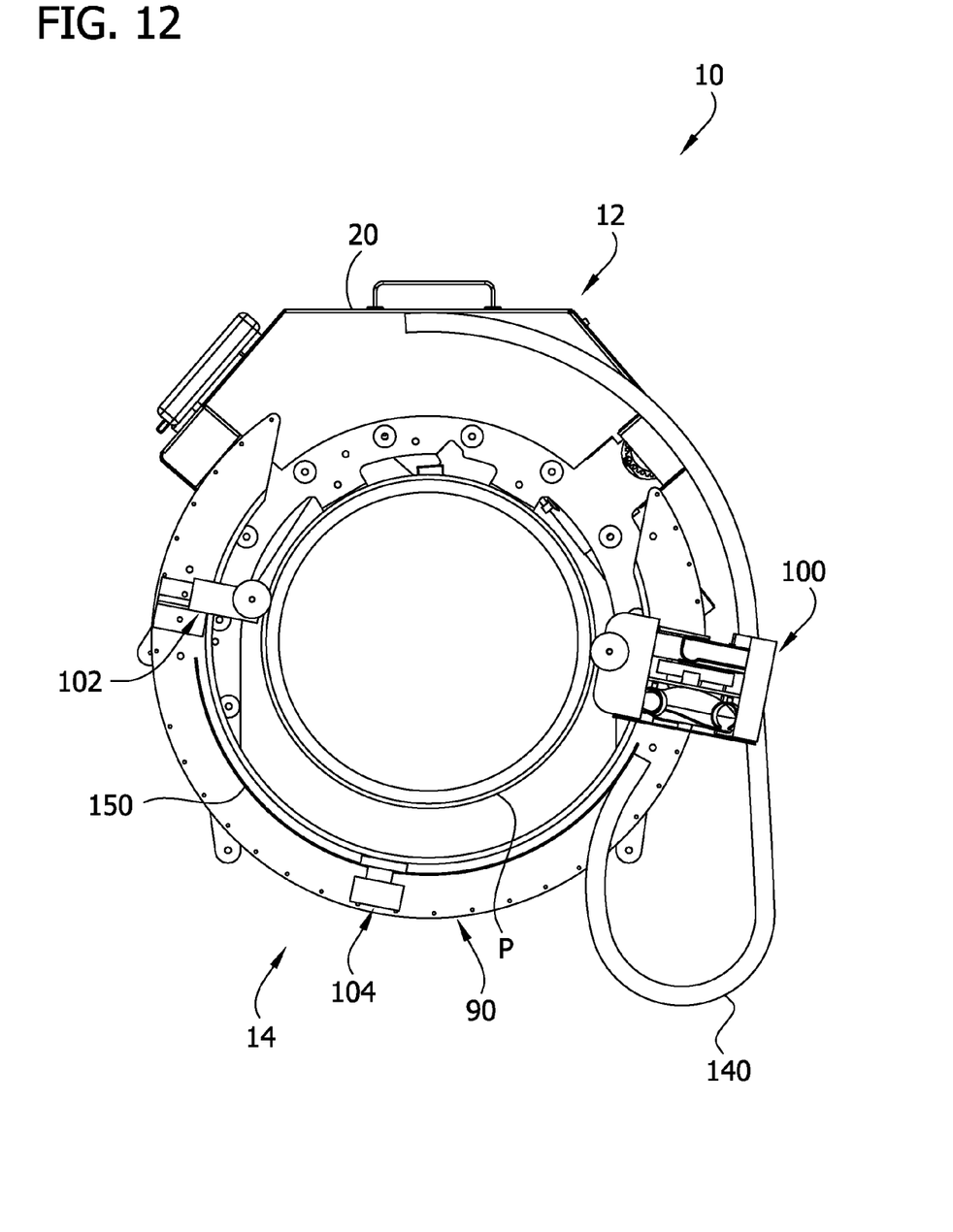
FIG. 12 is a view similar to FIG. 10 but showing the carriage rotated in a clockwise direction with respect to its home position.

The apparatus 10 generally includes a stationary base 12 adapted for securely engaging the pipe P and a carriage 14 mounted on the base for movement with respect to the base to turn back and forth around the pipe (e.g., see FIGS. 10-12). The carriage 14 turns around the pipe in a first direction (e.g., clockwise) and then a second direction (e.g., counterclockwise) to permit inspection of an entire circumference or at least a portion of the circumference of the pipe. As described in further detail below, the base 12 includes control components, a portable power source, various inspection gauges, and drive components for driving revolving motion of the carriage 14. The carriage 14 includes various inspection components used to inspect the outer surface of the pipe. In the view of FIG. 1, the base 12 is positioned behind or to the left of the carriage 14. The base 12 and carriage 14 are shown by themselves in FIGS. 3 and 6, respectively, and will be described in further detail below.

As shown in FIG. 1, the base 12 includes a shroud 20 for covering a variety of control and drive components. In FIG. 2, and in the majority of the remainder of the figures, the shroud 20 is removed for exposing interior components. A handle 22 is provided on top of the shroud 20 for assisting a user in carrying the apparatus 10 between inspection sites and in positioning the apparatus on a pipe section P to be inspected. As will become apparent, the apparatus 10 is configured to be mounted on the pipe by being set onto the pipe from a position above the pipe. The apparatus 10 may be removed from the pipe by raising it generally vertically off the pipe. To inspect several sections of the same pipe, the apparatus 10 is carried to and mounted on the separate sections of the pipe. After being mounted on a pipe section, the apparatus 10 may inspect the outer surface of the pipe at that section automatically, semi-automatically, or under substantial manual direction.

The apparatus 10 includes control actuators 24 such as buttons or switches positioned on an upper side of the shroud 20. The actuators 24 may be operative to power the apparatus 10 on/off, select between automatic and manual modes, and/or initiate an inspection step. The apparatus 10 may include a mobile computing device 26 (e.g., smart phone, tablet, or portable computer). In the illustrated embodiment, the device 26 is received in a mount on the shroud 20 for releasably securing the device on the base 12. The device 26 may include a microprocessor, data storage media, user data input interface (e.g., keypad or touch screen), communications interfaces (e.g., wired connection ports, wireless antennas, and modems), and/or GPS antenna. Data acquired, received, stored and/or processed by the mobile computing device 26 may be used in conjunction with inspection data collected by other devices on the base 12 and devices carried on the carriage 14. For example, the mobile computing device 26 may be used as a controller for receiving and executing inspection instructions and for collecting and logging inspection data from various inspection components of the apparatus 10.

Figure 3:
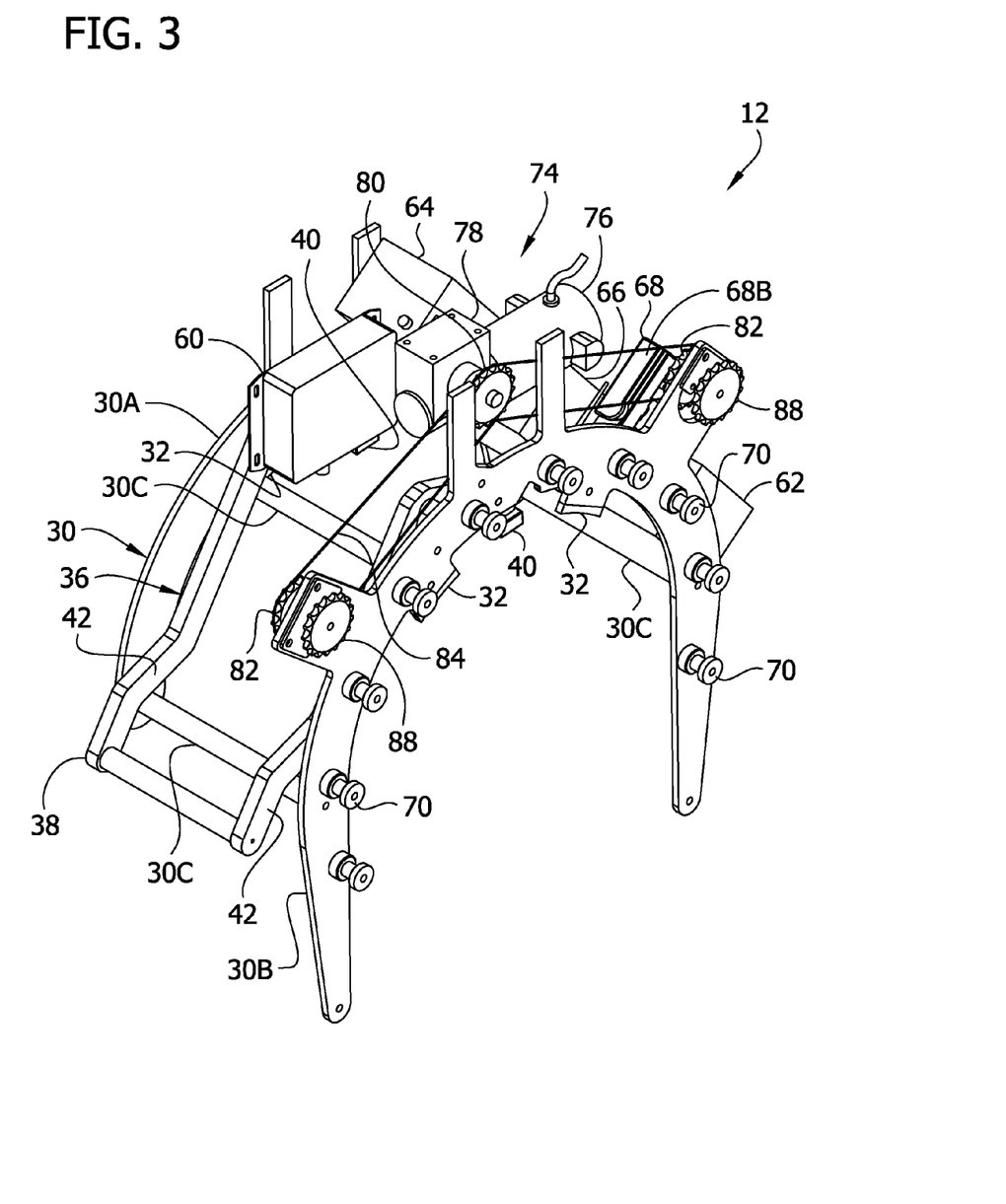
FIG. 3 is a front perspective of a base of the apparatus.

Referring now to FIG. 3, the base 12 includes a generally saddle-shaped frame 30 sized and shaped for straddling the pipe section P. The frame 30 includes a rear semi-circular frame member 30A and a front U-shaped frame member 30B providing the base with a mouth opening in a downward direction for being received over the pipe. The frame members 30A, 30B are connected to each other by a plurality of rungs 30C. Both of the frame members 30A, 30B include feet 32 protruding radially inward for engaging the pipe and supporting the base 12 on the pipe.

Figure 4:
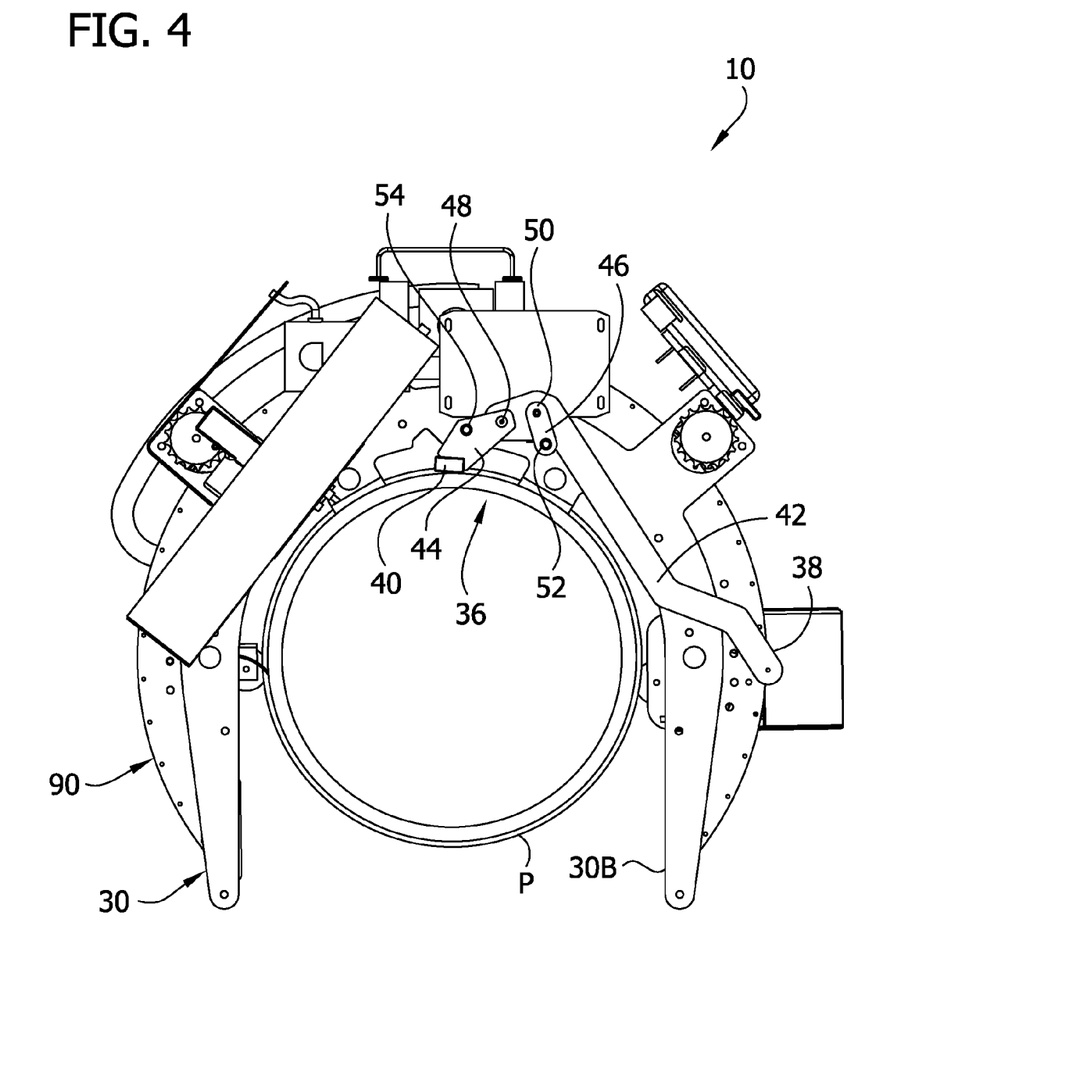
FIG. 4 is a rear elevation of the apparatus having a rear base frame member removed to expose a magnetic fastener engaged with the pipe for securing the base on the pipe section.
Figure 5:
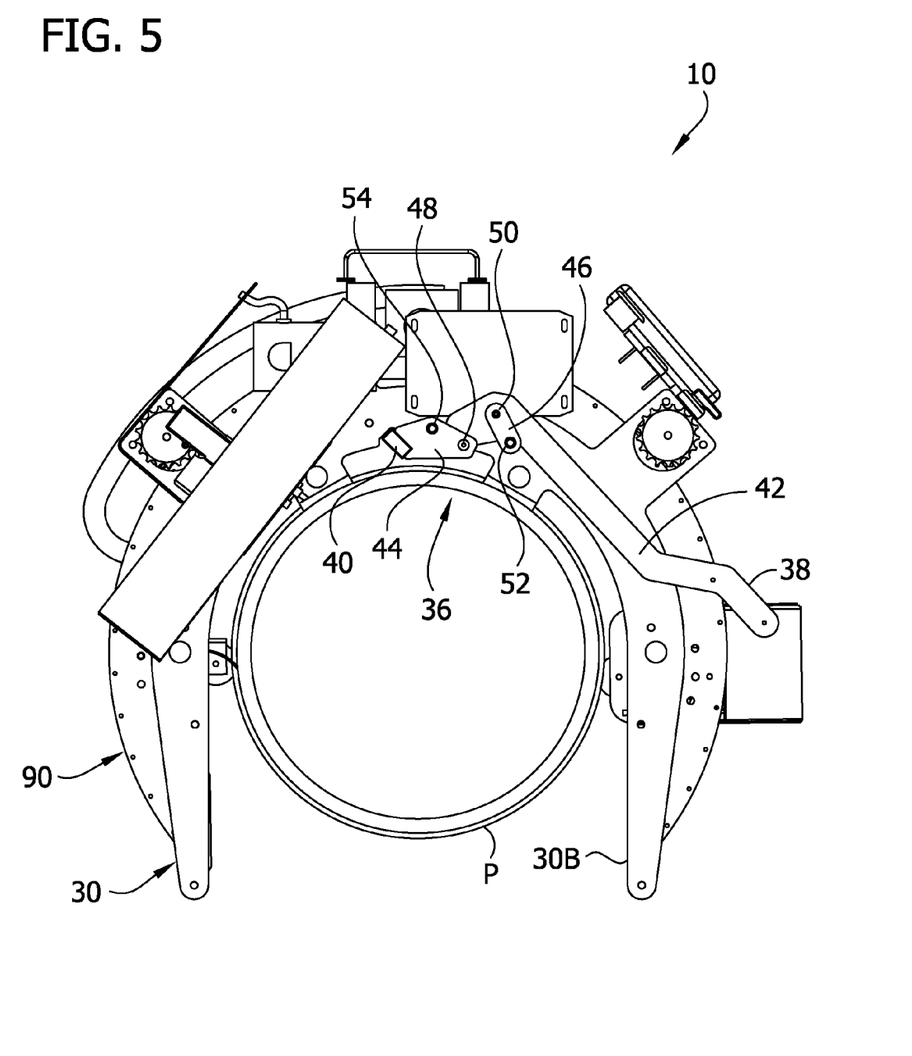
FIG. 5 is a view similar to FIG. 4 but showing the magnetic fastener disengaged from the pipe.

The base 12 includes a magnetic fastener 36 adapted for selectively securing the base in position on the pipe P. The fastener 36 includes a lever 38 pivotally connected to the frame 30 for engaging and disengaging a pair of ferromagnetic feet or magnets 40 with the outer surface of the pipe. When engaged with the pipe, the magnets 40 provide the equivalent of about 80 to 100 pounds of force acting to maintain the base 12 in position on the pipe. The magnets 40 are actuated by respective front and rear arms 42 of the lever 38. The fastener 36 is shown in closer detail in the views of FIGS. 4 and 5 in which the rear frame member 30A is removed to expose the rear side of the fastener. The fastener 36 is shown in a fastening position in FIG. 4 in which the magnets 40 are engaged with the pipe, and the fastener is shown in a non-fastening position in FIG. 5 in which the magnets are disengaged from the pipe. The fastener 36 includes an over-center pivot arrangement adjacent the proximal end of the lever 38 for moving the magnets 40 toward and away from the pipe. The arms 42 are connected to respective legs 44 and pivot bars 46 by non-fixed pivot connections 48, 50. The pivot bars 46 and feet are pivotally connected to respective frame members 30A, 30B by fixed pivot connections 52, 54. The arrangement is such that movement of the lever 38 tending to move its distal end radially away from the pipe causes the magnets 40 to disengage the pipe. The pivot connection 48 of the arm 42 and the leg 44 passes "over center" between the fixed pivot connections 52, 54 of the leg and pivot bar 46 to the frame 30, and in the "over center" position the magnets 40 are held by the linkage against the force of gravity and magnetic attraction away from the pipe. Accordingly, the base 12 may be selectively fastened to and unfastened from the pipe by actuating the lever 38 to engage and disengage the magnets 40 from the pipe. The secure connection of the base 12 to the pipe provides a stable platform for supporting the carriage 14 while it revolves around the pipe. Other means of securing the base 12 to the pipe may be used without departing from the scope of the present invention. For example, a strap may be connected to and tightened between opposite sides of the U-shaped frame member 30B below the pipe.

Figure 8:
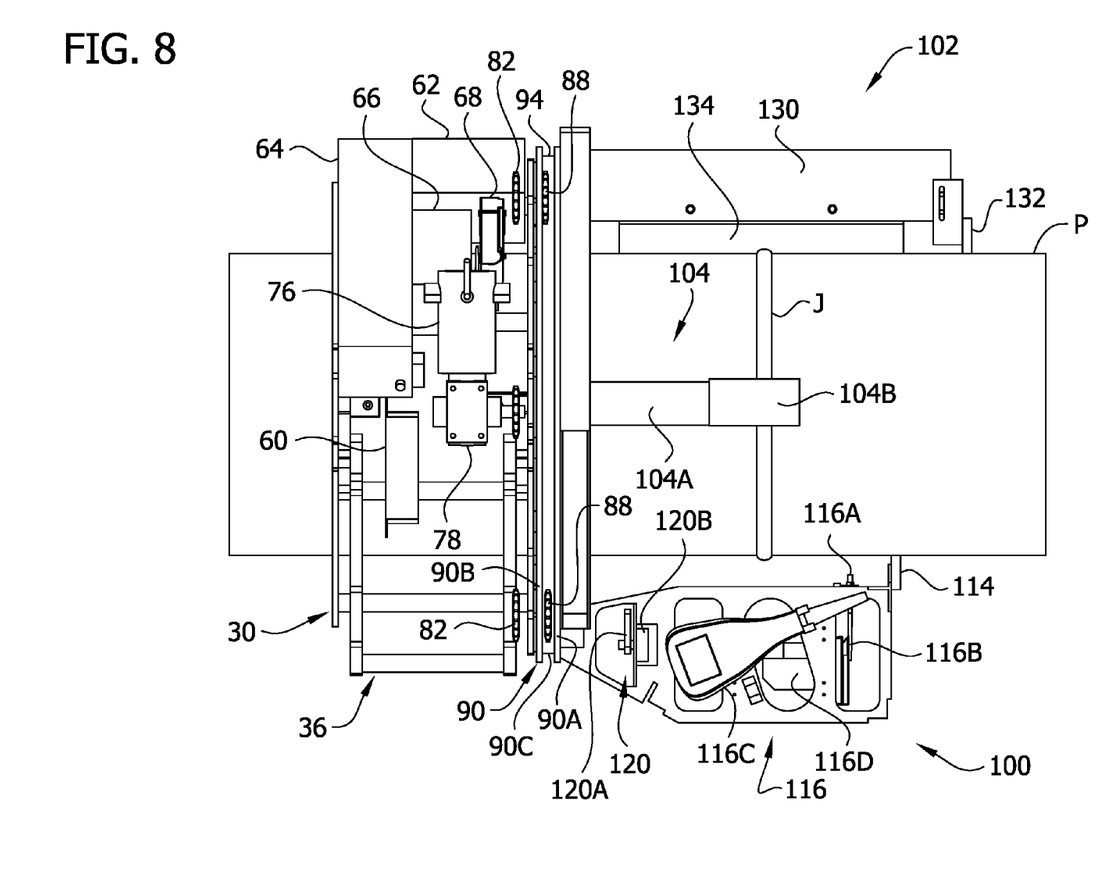
FIG. 8 is a top view of the apparatus and pipe section.
Figure 9:
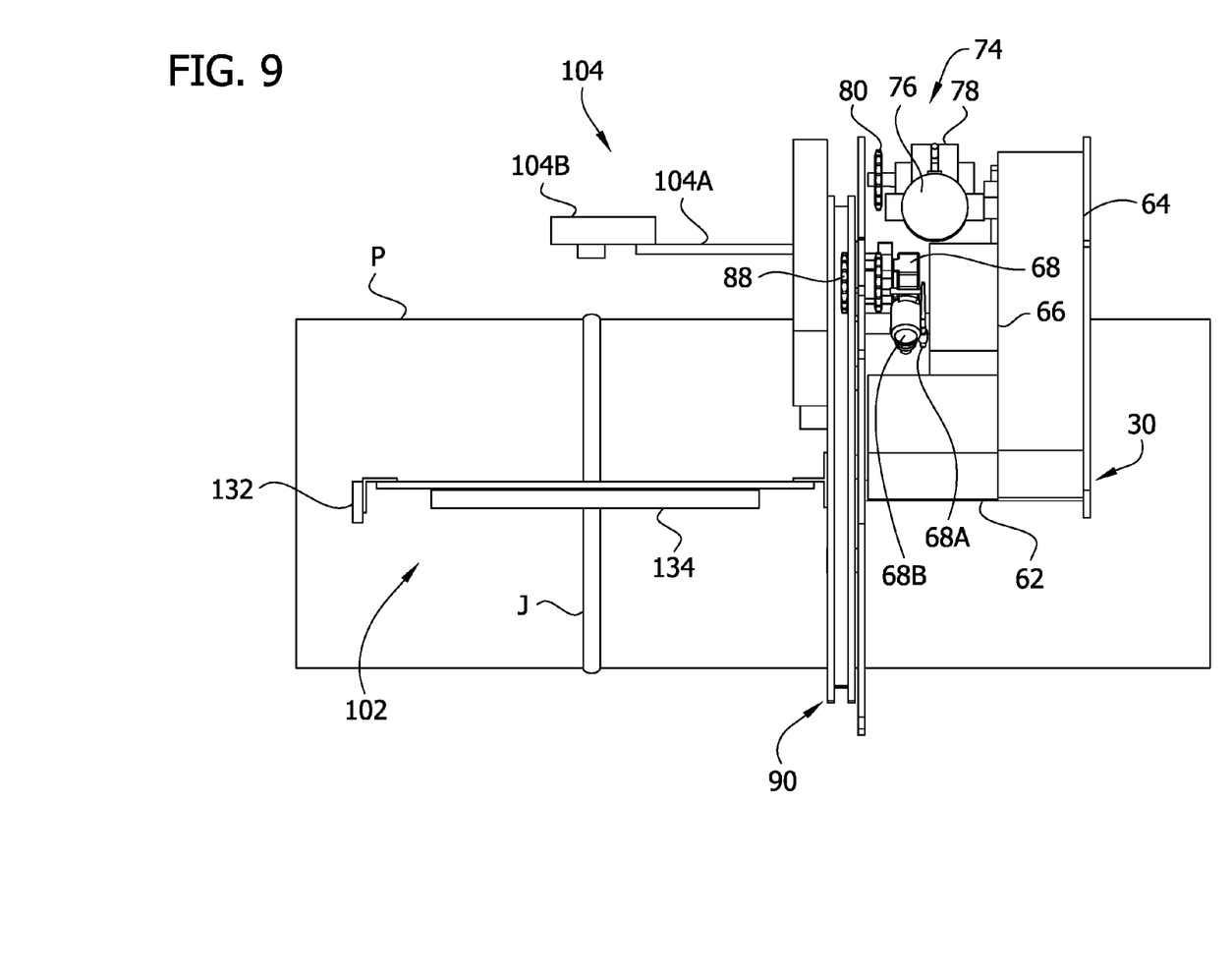
FIG. 9 is a right side view of the apparatus and pipe section.

Various control and inspection components are mounted on the base 12. These components are shown in FIG. 3, but may be better viewed in FIGS. 7, 8, and/or 9. For example, the base 12 may include an integral controller 60 for use in conjunction with the mobile computing device 26 and/or as a stand-alone controller. Like the mobile computing device 26, the controller 60 may include a microprocessor, data storage media, communications interfaces (e.g., wired connection ports, wireless antennas, and modems), and/or GPS antenna. The controller 60 is in operative communication with the actuators 24 (e.g., for receiving user-input regarding start/stop and/or manual/automatic modes). The base 12 includes a portable power source 62 (e.g., at least one battery) for powering the various electronic components of the inspection apparatus 10. The base 12 includes a holiday detection processor 64 in communication with a device carried by the carriage 14 as part of an electronic holiday detector, as explained in further detail below. The base 12 also includes an ambient condition gauge 66 and a pipe temperature gauge 68. The ambient condition gauge 66 may be adapted for sensing the ambient temperature and/or humidity adjacent the pipe. The pipe temperature gauge 68 is adapted for sensing the surface temperature of the pipe. As shown in FIG. 9, the pipe temperature gauge 68 includes a temperature probe 68A and an actuator 68B (e.g., a solenoid) for extending and retracting the probe radially with respect to the pipe for sensing its surface temperature and storing the probe in a retracted position. The holiday detection signal processor 64, ambient condition gauge 66, and pipe surface temperature gauge 68 are in operative communication with the controller 60 and/or mobile computing device 26 for transmitting signals representative of inspected characteristics for storage, transmission offsite, and/or analysis.

Referring again to FIG. 3, a plurality of bearings 70 protrude from the front face of the front U-shaped frame member 30B and collectively define a track along which the carriage 14 is movable for revolving around the pipe P. The bearings 70 each have a generally cylindrical outer surface including a circumferential groove spaced between front and rear ends of the bearings. The grooves of the bearings 70 collectively define a semi-circular segmented channel for receiving the carriage 14 and guiding rotation of the carriage. The bearings 70 may comprise lubricant-impregnated metal for facilitating the carriage 14 in gliding along the bearings. Alternatively, the bearings may comprise rollers. Other bearings may be used without departing from the scope of the present invention.

The base 12 includes a carriage drive system 74 for turning the carriage 14 back and forth on the pipe (e.g., see also FIGS. 10-12). Referring to FIG. 3, in the illustrated embodiment, the drive system 74 includes a motor 76, a gear box 78, and a chain and sprocket assembly. The motor 76 drives a primary sprocket 80 via the gear box 78, which in turn rotates secondary sprockets 82 via a loop of chain 84 meshed with the three sprockets. The chain 84 is represented schematically in FIG. 3. The secondary sprockets 82 are connected to carriage drive sprockets 88 by respective shafts passing through ears extending from the front frame member 30B. The drive sprockets 88 are positioned in the same plane as the channel defined by the bearings 70. When the motor 76 is energized, the chain and sprocket assembly causes rotation of the carriage drive sprockets 88, which engage and drive the carriage 14 along the bearings 70 about the circumference of the pipe. Other types and configurations of carriage drive systems may be used without departing from the scope of the present invention. For example, a geared system may be used, and a direct drive system may be used instead of an indirect drive system.

Figure 6:
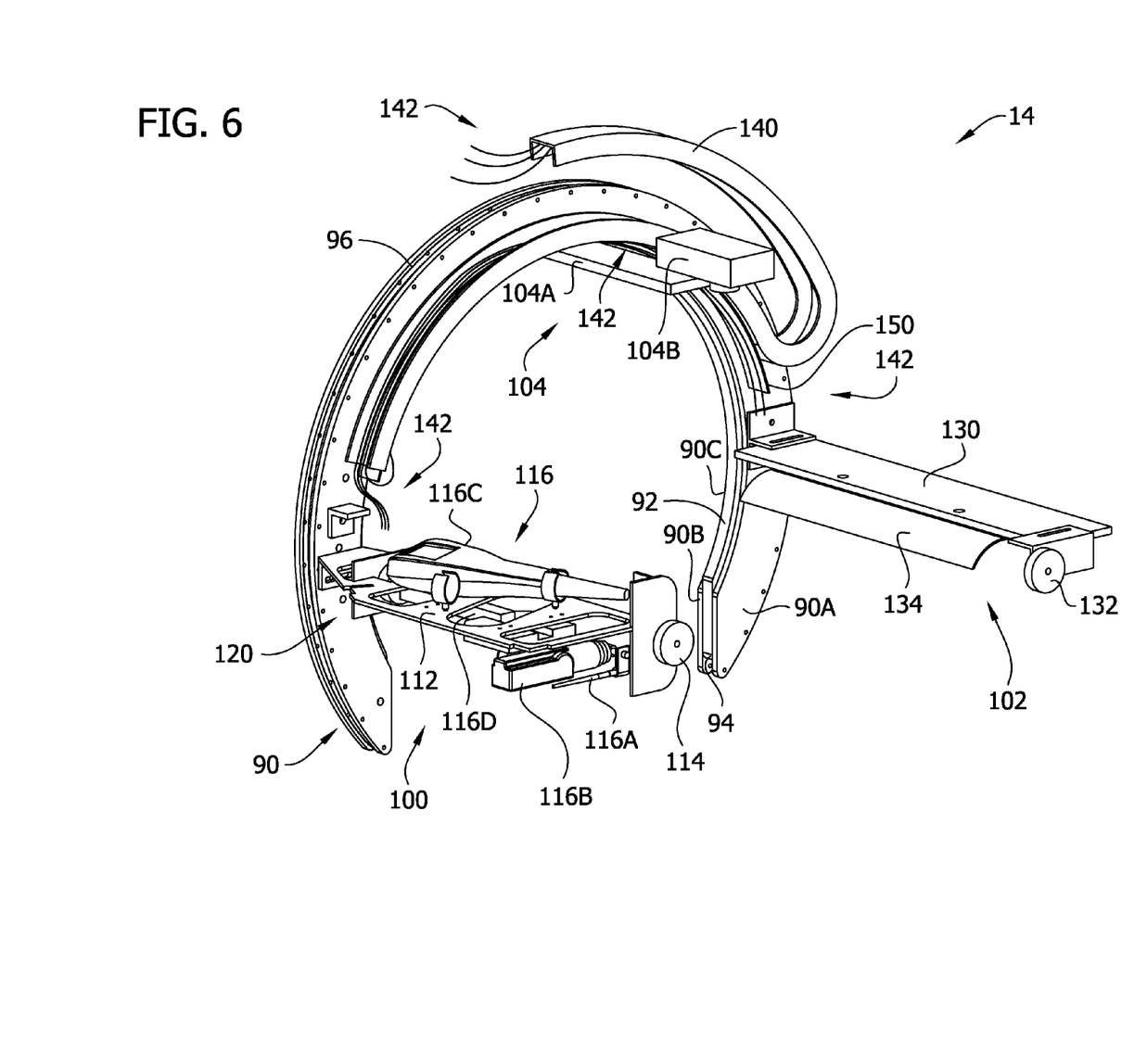
FIG. 6 is a front perspective of a carriage of the apparatus.

Referring to FIG. 6, the carriage 14 includes a semicircular frame 90 providing the carriage with a mouth facing downward for being received over the pipe. The frame 90 includes three C-shaped frame members including a front frame member 90A, a rear frame member 90B, and an intermediate frame member 90C sandwiched by the front and rear frame members. The inner edge of the intermediate frame member 90C extends radially inboard of the inner edges of the front and rear frame members 90A, 90B, providing the frame 90 with a radially inward protruding rib 92. The rib 92 is sized and shaped for reception in the segmented semi-circular channel formed by the bearings 70 of the base 12. The rib 92 serves as a guide for guiding the carriage frame 90 along the channel and maintaining it on the base 12. The outer edges of the front and rear frame members 90A, 90B extend radially outboard of the outer edge of the intermediate frame member 90C, providing the frame with a radially outward facing channel 94. A length of chain 96 (broadly "drive system engaging member") represented schematically in FIG. 6 is received in the channel 94. The chain 96 is adapted for engagement with the carriage drive sprockets 88 on the base 12. Rotation of the carriage drive sprockets 88 causes the carriage frame 90 to move along the bearings 70, as described in further detail below. Other drive system engaging members may be provided on the carriage 14 without departing from the present invention. For example, instead of the chain 96, the frame 90 may include a plurality of teeth resembling a geared surface. Moreover, the drive system engaging member may comprise a smooth or knurled surface for frictional engagement with drive rollers of the carriage drive system.

The carriage frame 90 includes inspection head mounting portions on opposing sides of the frame. In the illustrated embodiment, two inspection heads 100, 102 are mounted on the opposing sides of the frame 90, and a third inspection head 104 is mounted on an intermediate portion of the frame. The first and second inspection heads 100, 102 are mounted at positions generally diametrically opposed from one another. Such an arrangement improves balance of the carriage 14. In use, these inspection heads 100, 102 would be positioned on opposing sides of the pipe P and promote balanced turning of the carriage 14 on the pipe. The carriage 14 is modular in that one or more of a variety of inspection heads may be mounted on the frame 90 for turning on the pipe. It will be understood that although three inspection heads 100, 102, 104 are shown, given the modular nature of the apparatus 10, one or more (e.g., four, five, etc.) inspection heads may be mounted on the carriage frame 90 at any given time depending on the inspection tasks desired to be completed. For example, if the apparatus 10 is being used to inspect surface profile prior to coating, a single surface profile inspection head 100 may be used. On the other hand, if the apparatus 10 is being used to inspect a coating for thickness and holidays, a coating thickness inspection head 100 and a holiday inspection head 102 may both be mounted on the carrier frame 90. In either scenario, a camera inspection head 104 may be mounted on the carrier frame 90 for collecting video or still photo image data representative of the area inspected. The camera inspection head 104 includes a support arm 104A and a camera 104B positioned for viewing at least the circumferential section of the pipe over which the other inspection heads 100, 102 travel. The camera 104B may include a fisheye lens to provide a wider field of view. Some inspection processes are complemented by visual inspection to visually identify characteristics such as color irregularity (e.g., rust) or burs. Image data from the camera 104B can be logged and correlated with other inspection data to permit remote or later visual inspection of areas identified as being problematic by other inspection heads 100, 102.

Figure 7:
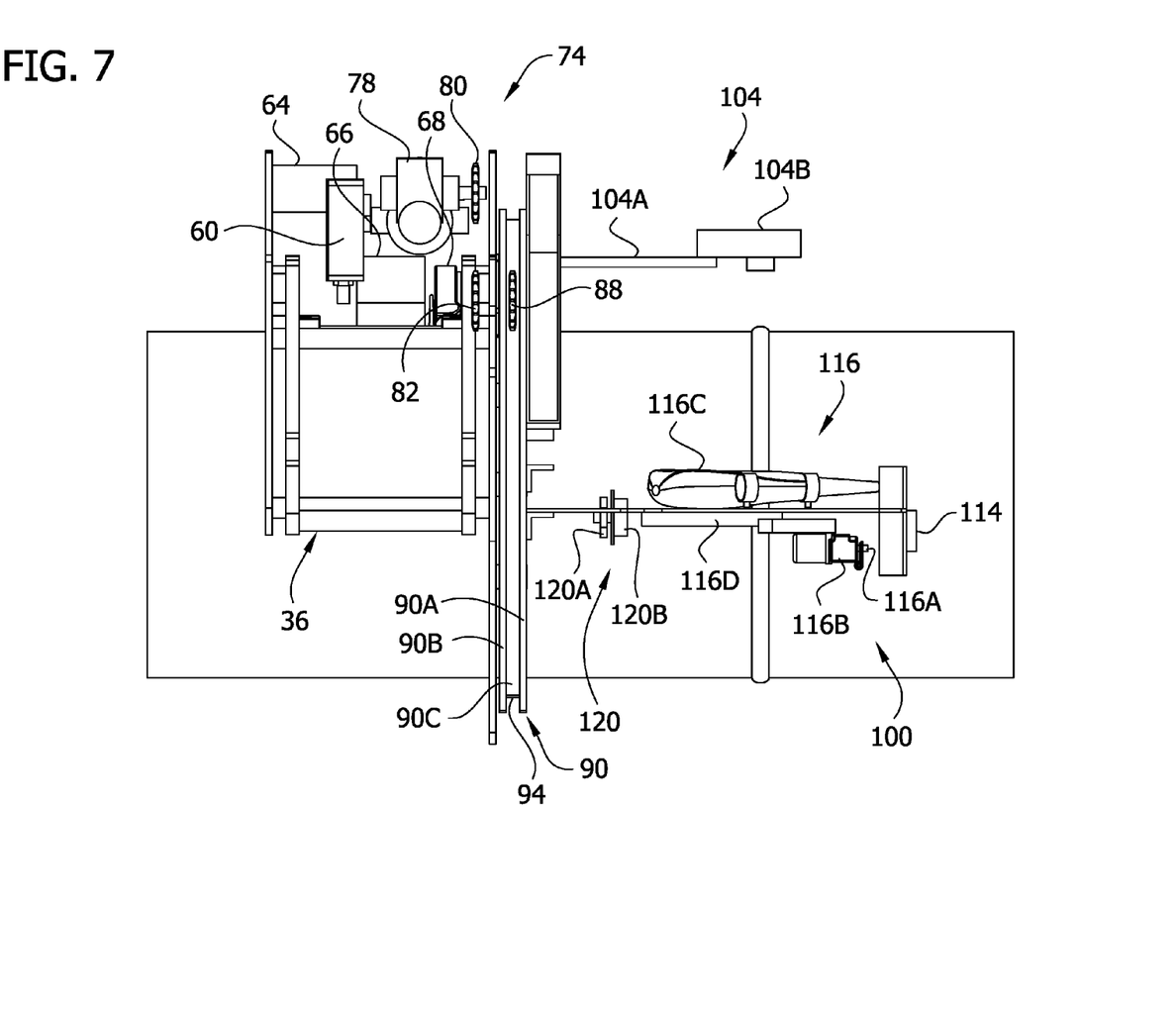
FIG. 7 is a left side elevation of the apparatus mounted on the pipe section.

The apparatus 10 as shown in FIG. 2 is configured for inspecting a pipe coating for thickness and holidays. The first inspection head 100 may be adapted for inspecting coating thickness. A shroud 110 of the inspection head is shown in FIG. 1 but is removed in the majority of the other figures, including FIG. 2, to show internal components. Referring again to FIG. 6, the inspection head 100 includes an elongate shelf 112 extending from a first end connected to the carriage frame 90 to an opposite end including a ferromagnetic wheel 114. The ferromagnetic wheel 114 is magnetically attracted to the pipe and thus improves the stability of the shelf 112 by supporting the distal end of the otherwise cantilevered shelf in position with respect to the pipe. The wheel 114 permits the shelf 112 to have a length sized to span a significant section of the pipe yet maintain stability even when the carriage 14 is moving quickly. The wheel 114 is rotatably mounted to the shelf 112 for rolling along the surface of the pipe as the carriage 14 moves. An electronic coating thickness gauge 116 is mounted on the shelf 112. The coating thickness gauge 116 includes a probe 116A supported below the shelf 112 on an actuator 116B (e.g., a solenoid) adapted for moving the probe radially with respect to the pipe. For example, the probe 116A may be adapted for induction, magnetic, or Hall effect testing to determine coating thickness. The radial actuator 1166 moves the probe 116A near or into engagement with the surface of the pipe when turning of the carriage 14 is paused. The coating thickness gauge 116 includes a processor 116C supported above the shelf 112 for processing signals from the probe 116A. Processed signals representative of coating thickness are transmitted to the controller 60 or mobile computing device 26. The coating thickness gauge 116 also includes an axial actuator 116D adapted for moving the probe 116A axially with respect to the pipe. Accordingly, the probe 116A may measure coating thickness at various axial positions along the pipe as well as at different circumferential portions of the pipe. For example, the probe 116A is shown in FIG. 7 positioned to a right side of the joint J. The axial actuator 116D may be used to move the probe 116A closer to the joint J and/or to the other side of the joint. The controller 60 may be programmed to sample the coating thickness at standard positions (e.g., circumferential positions corresponding to 12, 3, 6, and 9 o'clock) and/or random positions. This increases the inspection thoroughness and reliability compared to manual execution of the inspection. For example, if coating thickness is determined by the gauge 116 to be out of specification in a certain area or almost out of specification, the frequency or density of testing in that area may be automatically increased to assist in determining the extent of the problem.

The first inspection head 100 also includes a circumferential position indicating device 120 for indicating the circumferential position of the inspection head 100 with respect to the pipe P. In the illustrated embodiment, the device 120 includes a pendulum 120A operatively connected to an encoder 120B. The pendulum 120A is best viewed in FIGS. 7 and 8. The pendulum 120A pivots with respect to the encoder 120B as the carriage 14 rotates around the pipe so that the pendulum consistently hangs in a generally downward orientation. The encoder 120B documents the angular position of the pendulum 120A to determine circumferential position with respect to the pipe. This information is transmitted to and may be logged by the controller 60 and/or mobile computing device 26. Correlating the circumferential position information with inspection data gathered, for example, from the coating thickness probe 116A, in combination with GPS position information may be used to relatively precisely pinpoint the location on the pipe where inspection data (e.g., indicating a problem or need for further inspection) was acquired. The encoder 120B may be used for determining circumferential position of any inspection component (e.g., of other inspection heads) mounted on the carriage 14 and for correlating data collected by those components to specific circumferential positions on the pipe assuming a position of the inspection component is known with respect to the encoder. Other types of circumferential position indicating devices may be used without departing from the scope of the present invention. For example, an accelerometer or an encoder operatively connected to the motor may be used.

Referring again to FIG. 6, the second inspection head 102 is adapted for inspecting pipe coating for holidays. Holidays are discontinuities in the coating such as small holes or other irregularities providing a passageway to the pipe surface. The inspection head 102 includes a non-conductive insulator 130 in the shape of a bar extending from a first end connected to the carriage frame 90 to an opposite end including a ferromagnetic wheel 132. The ferromagnetic wheel 132 operates in the same fashion and provides the same benefits described above with respect to the first inspection head 100. In this case, the ferromagnetic wheel 132 is particularly useful because inspection data is collected while the carriage 14 is moving, making stability of inspection head 102 during movement even more relevant. A conductive tongue 134 extends along the length of the insulator 130 and protrudes into engagement with the pipe coating. As the carriage 14 rotates, the tongue 134 wipes along the circumference of the pipe. The tongue 134 may comprise a continuous flap or a brush including materials such as neoprene rubber, copper, stainless steel, or nylon. The tongue 134 has a length sufficient to engage the pipe across a span including the pipe joint J and end margins of the joined pipes on opposite sides of the joint. The tongue 134 desirably conforms to a raised or otherwise irregular profile of the joint J for detecting holidays not only on the surfaces of the joined pipes but also at the joint. The circumferential position of the tongue 134 with respect to the pipe surface can be adjusted by changing the mounting points of the wheel 132 and carriage frame 90 on the insulator 130. The tongue 134 is in operative communication with the holiday detection processor 64 on the base 12. A ground wire may extend from the processor 64 to ground such that changes in current field may be detected. Current from the tongue 134 seeks a pathway to the pipe surface, but the coating acts as an insulator. Defects in the coating provide a pathway for the electrical current to "burn through" to the pipe and indicate to the presence of the defects to the processor. Like with the coating thickness gauge 116, inspection data from the electronic holiday detector is delivered to the controller 60 and/or mobile computing device 26 for transmission, logging, and/or analysis. The encoder 120B may be used to indicate circumferential positioning of detected holidays.

The first inspection head 100 may alternatively be described as being adapted for inspecting a blasted surface profile or anchor profile of the pipe prior to coating. The configuration described above of head 100 would be substantially the same in this case except that the gauge 116 includes a probe 116A adapted for measuring the thickness of coating on the pipe surface. In this case, the probe 116A may include a pin or anvil adapted for engaging the pipe surface for measuring "peaks" and "valleys" to determine the surface profile of the pipe. The radial actuator 116B moves the probe into engagement with the surface of the pipe when turning of the carriage 14 is paused. The actuators 116B, 116D may be used in a similar fashion as described above for sampling the surface profile at various positions along the pipe section. If the surface profile is determined by the gauge 116 to be out of specification or almost out of specification in a certain area, the frequency or density of testing in that area may be automatically increased to assist in determining the extent of the problem.

Referring again to FIG. 6, the carriage 14 includes a cable guard 140 adapted for protecting cables 142 (shown schematically in FIG. 6) which may connect components of the base 12 with components of the carriage. For example, gauges 116 on the carriage 14 may require wired power to be supplied to the actuators 116B, 116D or the probes 116A. Moreover, a cable extending from the base 12 to the tongue 134 of the holiday detector may be required for supplying electrical current to the tongue. The cable guard 140 is a snake-like member which is flexible at least in the plane in which the carrier revolves around the pipe. A proximal end of the cable guard 140 is connected to a front side of the shroud 20 of the base 12 (see FIG. 1). A distal end of the cable guard 140 is positioned radially inboard from the first end and connected to the carrier frame 90 adjacent the first inspection head 100. Cables 142 from the cable guard 140 leading to the first inspection head 100 exit the cable guard near the first inspection head. Cables 142 from the cable guard 140 leading to the second inspection head 102 exit the cable guard at about the same position as the other cables, but then extend along the carriage frame 90 to the second inspection head. The ends of the cable guard 140 may be pivotally connected to the base 12 and carriage 14. The cable guard 140 may include generally rigid segments connected to each other for pivoting movement in the plane in which the carriage 14 revolves but for preventing substantial pivoting movement in a direction laterally with respect to the plane. Alternatively, the cable guard 140 may comprise a generally flexible material, such as a piece of flexible conduit or channel. The cable guard 140 may be tubular or channel-shaped. In the illustrated embodiment, the cable guard 140 is shown schematically as a continuous channel.

The cable guard 140 is adapted for changing its configuration (e.g., overlap or amount of fold) corresponding to movement of the carriage 14. The length of the cable guard 140 between its connection points to the base 12 and carriage 14 is free of fixed connection and is thus free to change orientation. A cable guard support 150 in the form of a semi-circular shelf protrudes from the front surface of the carrier frame 90. The cable guard 140 may engage or disengage this support 150 depending on the rotational position of the carriage 14. In FIGS. 1, 2, and 10, the carriage 14 is shown in a "home" position with respect to the base 12. In this position, the mouths of the base and carriage frames 30, 90 are in register with each other for receiving the base 12 and carriage 14 over the pipe section. In the home position, a distal portion of the cable guard 140 is supported on the cable guard support 150, and an intermediate portion of the cable guard overlaps itself, defining a fold where it turns from a first circumferential direction to an opposite circumferential direction with respect to the pipe. To move the inspection heads 100, 102, 104 mounted on the carriage frame 90 a sufficient amount to inspect the entire circumference of the pipe section, the carriage 14 needs to be adapted for turning a cumulative total of at least 360 degrees from the home position. In the illustrated embodiment, the cable guard 140 is sized for permitting the carriage 14 to rotate in a clockwise direction (see FIG. 12) and a counter-clockwise direction (see FIG. 11) from the home position more than about 180 degrees each direction (e.g., about 190 to 200 degrees each direction). The cable guard 140 may permit less of an extent of rotation (e.g., non-overlapping) without departing from the scope of the present invention. However, it is desirable that at least a slight overlap in the range of movement of the inspection heads 100, 102, 104 be provided to cover the entire circumference of the pipe. The controller 26, 60 may control rotation reversal based on signals from the encoder 120B. It will be appreciated that the carriage 14 has a length sufficient to span the lower gap in the semi-circular channel formed by the bearings 70 and to remain in engagement with at least one carriage drive sprocket 88 at all times. As shown in FIG. 11, when the carriage 14 rotates in a first circumferential direction around the pipe P (e.g., counterclockwise), the overlap of the cable guard 140 tends to decrease, and the fold in the cable guard may unfold. As shown in FIG. 12, when the carriage 14 rotates in an opposite circumferential direction around the pipe (e.g., clockwise), the overlap tends to increase initially, and the fold is maintained. Moreover, the distal end of the cable guard 140 tends to disengage the cable guard support 150 and may completely disengage it. The configuration is such that the cable guard 140 and cable guard support 150 protect the cables 142 from interfering with the carriage drive system 74 or being pinched, kinked, or severed during movement of the carriage 14.

As is now apparent, in use, an operator mounts desired inspection heads 100, 102, 104 on the carriage 14, mounts the apparatus 10 on a pipe section P, and initiates inspection of the pipe section. The carriage 14 turns back and forth on the pipe section to collect data such representative of surface profile, coating thickness, or coating voids. Visual data such as video and/or still photography may also be collected. Temperature of the pipe and ambient humidity and temperature may be determined. All of the collected data may be logged, transmitted, and/or analyzed, such as by the mobile computing device 26, for readily determining deviations from required specifications more accurately and more reliably than previously possible. When inspection of a pipe section is complete, the user may carry the apparatus 10 to another pipe section and repeat the inspection process.

It will be appreciated that the modularity and automation or semi-automation of the inspection tasks accomplished by the apparatus 10 provides multiple benefits over conventional inspection methods. Inspection consistency and thoroughness is improved, and inspection may be more reliable than a person manually attempting inspection. For example, a person is less likely to sample various circumferential positions of a pipe when difficult to reach (e.g., the underside of the pipe, or the far side of the pipe). The apparatus 10 permits automated logging of various types of inspection data and correlation of that data. For example, temperature (pipe and/or ambient), humidity, surface profile, coating thickness, coating discontinuity, and photographic or video inspection data may be gathered all by the apparatus 10 more precisely than previously possible and in a form in which problem areas and trends can be readily identified based on precise position information (e.g., GPS position and circumferential position on the pipe section inspected). The position information may be used to map collected inspection data and to authenticate inspection performance. These capabilities of the apparatus 10 will provide pipeline owners with increased assurance that coating preparation and application were performed to specification and will ultimately increase the lifespan of pipelines because they will be better coated as a result of better inspection.

Having described the invention in detail, it will be apparent that modifications and variations are possible without departing from the scope of the invention defined in the appended claims.

As various changes could be made in the above constructions and methods without departing from the scope of the invention, it is intended that all matter contained in the above description and shown in the accompanying drawings shall be interpreted as illustrative and not in a limiting sense.

What is claimed is:

1. An outer pipe surface inspection apparatus comprising:
   a base configured for mounting on the outer surface of the pipe;
   a carriage mounted on the base and configured to move with respect to the base generally along a circumference of the pipe;
   a carriage drive system connected to the carriage and configured to drive movement of the carriage on the base;
   a surface profile inspection head mounted on the carriage configured to inspect a surface profile of the outer pipe surface;
   a camera inspection head mounted on the carriage;
   a circumferential position sensor mounted on the carriage configured to sense a circumferential position of the carriage with respect to the pipe;
   a controller operatively connected to the carriage drive system, the surface profile inspection head, the camera inspection head, and the circumferential position sensor, the controller being programmed to control movement of the carriage on the base and control operation of the inspection heads.

2. An outer pipe surface inspection apparatus as set forth in claim 1 wherein the controller is programmed to correlate circumferential position data from the circumferential position sensor with inspection data from the surface profile inspection head and the camera inspection head.

3. An outer pipe surface inspection apparatus as set forth in claim 1 wherein the controller is programmed with instructions to operate the carriage drive system to move the surface profile inspection head to locations spaced around a circumference of the outer pipe surface and to operate the surface profile inspection head to inspect surface profile on the outer pipe surface at the locations.

4. An outer pipe surface inspection apparatus as set forth in claim 3 wherein the controller is programmed with instructions to, in response to detecting a surface profile outside a predetermined specification, move the surface profile inspection head to additional locations on the outer pipe surface and to operate the surface profile inspection head to inspect the outer pipe surface at the additional locations.

5. An outer pipe surface inspection apparatus as set forth in claim 1 wherein the surface profile inspection head includes a probe adapted to measure the surface profile on the outer pipe surface and a actuator configured to move the probe into engagement with the outer pipe surface.

6. An outer pipe surface inspection apparatus as set forth in claim 1 wherein the surface profile inspection head includes a ferromagnetic wheel configured to engage and roll along the outer pipe surface.

7. An outer pipe surface inspection apparatus as set forth in claim 1 wherein the circumferential position sensor includes an encoder.

\* \* \* \* \*